(12) United States Patent
Harding

(10) Patent No.: US 7,901,136 B2
(45) Date of Patent: Mar. 8, 2011

(54) METHODS AND SYSTEM FOR CALIBRATING AND CORRECTING A DETECTION SYSTEM

(75) Inventor: Geoffrey Harding, Hamburg (DE)

(73) Assignee: Morpho Detection, Inc., Newark, CA (US)

( * ) Notice: Subject to any disclaimer, the term of this patent is extended or adjusted under 35 U.S.C. 154(b) by 111 days.

(21) Appl. No.: 12/274,231

(22) Filed: Nov. 19, 2008

(65) Prior Publication Data

US 2010/0124315 A1 May 20, 2010

(51) Int. Cl.
*G01D 18/00* (2006.01)
*G01N 23/20* (2006.01)
*G01N 23/201* (2006.01)

(52) U.S. Cl. .............................. 378/207; 378/71; 378/86
(58) Field of Classification Search .................. 378/70, 378/86, 87, 88, 92, 119, 121, 124, 134, 204, 378/205, 207, 210
See application file for complete search history.

(56) References Cited

U.S. PATENT DOCUMENTS

| | | | |
|---|---|---|---|
| 4,803,711 A | 2/1989 | Tsujii et al. | |
| 5,469,429 A | 11/1995 | Yamazaki et al. | |
| 5,550,886 A | 8/1996 | Dobbs et al. | |
| 5,706,326 A | 1/1998 | Gard | |
| 5,974,111 A * | 10/1999 | Krug et al. ....................... | 378/57 |
| 6,185,275 B1 | 2/2001 | Toth et al. | |
| 6,862,336 B2 | 3/2005 | Nishide et al. | |
| 6,947,520 B2 * | 9/2005 | Yokhin et al. .................... | 378/70 |
| 7,001,071 B2 | 2/2006 | Deuringer et al. | |
| 7,056,020 B2 | 6/2006 | Saunders et al. | |
| 7,286,644 B2 | 10/2007 | Andrews | |
| 7,409,043 B2 | 8/2008 | Dunham et al. | |
| 7,447,297 B2 | 11/2008 | Dunham et al. | |
| 7,481,579 B2 * | 1/2009 | Yokhin et al. .................. | 378/207 |
| 7,600,916 B2 * | 10/2009 | Yokhin et al. .................. | 378/205 |
| 2005/0105685 A1 | 5/2005 | Harding | |
| 2007/0025512 A1 * | 2/2007 | Gertsenshteyn et al. ....... | 378/86 |
| 2008/0037713 A1 | 2/2008 | Andrews et al. | |
| 2008/0265167 A1 * | 10/2008 | Laurence et al. ........ | 250/363.09 |

OTHER PUBLICATIONS

Brunetti, et al., Abstract of Angular Calibration in Energy Dispersive X-ray Diffraction by Using Genetic Algorithms, 2009, Journal of X-ray Science and Technology, IOS Press, vol. 17, No. 3, pp. 253-264.*
PCT/US2009/065081, International Search Report and Written Opinion dated Jun. 14, 2010, 14 pages.
Hubbard, Camden R., "Certification of Si Powder Diffraction Standard Reference Material 640a", Journal of Applied Crystallography, vol. 16, Jun. 1, 1983, Denmark, pp. 285-288.
Toraya, Hideo et al., "Simultaneous Peak-Shift Correction in the Least-Squares Determination of Unit-Cell Parameters of a Sample with Standard Reference Material", Journal of Applied Crystallography, vol. 23, Aug. 1, 1990, Denmark pp. 282-285.

(Continued)

*Primary Examiner* — Edward J Glick
*Assistant Examiner* — Anastasia Midkiff
(74) *Attorney, Agent, or Firm* — Armstrong Teasdale LLP

(57) ABSTRACT

A method for calibrating a detection system including a multi-focus X-ray source includes performing a scan of a calibration material using the detection system to acquire scan data, determining a diffraction profile of the calibration material using the scan data, deriving an actual scatter angle using the determined diffraction profile, deriving an offset angle using the determined actual scatter angle, storing the derived offset angle, and generating a table including the stored offset angle.

20 Claims, 4 Drawing Sheets

OTHER PUBLICATIONS

Razik N.A., "Use of a Standard Reference Material for Precise Lattice Constant Determination of Materials of Cubic Crystal Structure", Journal of Materials Science Letters UK, vol. 7, No. 6, Jun. 1988, pp. 569-571.

Al-Heniti S. et al., "Lattice Thermal Expansion of CdTe0.9Se0.1 Solid Solution", Journal of Alloys and Compounds, vol. 387, No. 1-2, Jan. 25, 2005, pp. L5-L7.

G. Berti, M. D'Acunto, U. Bartoli, F. De Marco, "Calibration of Diffractometers II: Internal Consistency and the Balance", International Centre for Diffraction Data 2003, Advances in X-ray Analysis, vol. 46, pp. 270-277, Proceedings of the 51st Annual Denver X-Ray Conference Program, Colorado Springs, Colorado, USA Jul. 28-Aug. 2, 2002.

Yang Leng, "X-Ray Diffraction Methods", Chapter 2, Materials Characterization: Introduction to Microscopic and Spectroscopic Methods, John Wiley & Sons, Singapore, Copyright 2008, pp. 45-77.

G. Harding, "X-ray Diffraction Imaging-A Multi-Generational Perspective", Applied Radiation and Isotopes, vol. 67, No. 2, 2009, pp. 287-295.

* cited by examiner

METHODS AND SYSTEM FOR CALIBRATING AND CORRECTING A DETECTION SYSTEM

BACKGROUND OF THE INVENTION

1. Field of the Invention

The embodiments described herein relate generally to X-ray diffraction imaging systems and, more particularly, to a method to calibrate and correct for inaccuracies in X-ray source focus point positions.

2. Description of Prior/Related Art

At least some known security detection systems are used at travel checkpoints to inspect carry-on and/or checked bags for contraband, such as concealed weapons, narcotics, and/or explosives. Further, at least some of these known security detection systems include X-ray imaging systems. In an X-ray imaging system, an X-ray source transmits X-ray radiation through a container, for example a suitcase, towards a detector. The detector outputs are processed to identify a set of objects and/or materials in the container. In addition, at least some known X-ray imaging systems used in security detection systems include X-ray diffraction imaging (XDI) systems. At least some known XDI systems use inverse fan-beam geometry (a large source and a small detector) and a multi-focus X-ray source (MFXS). Further, at least some known XDI systems provide an improved discrimination of materials, as compared to that provided by other known X-ray imaging systems, by measuring d-spacings between lattice planes of micro-crystals in materials to perform an X-ray diffraction analysis. X-ray diffraction may yield data from a molecular interference function that may be used to identify other materials, such as liquids, in a container.

In at least some known XDI systems having an MFXS, all focus point positions of the MFXS should lie along a straight line in the a scan plane to generate an optimal X-ray diffraction image. The focus point positions are, however, in practice affected by manufacturing inaccuracies and/or thermo-mechanical effects, such as expansion. As such, the focus point positions in known XDI systems do not lie along a straight line but, rather, are offset from the straight line by varying distances. Such offsets cause the focus point positions to be inaccurate. Inaccuracies of the focus point positions in an MFXS system may cause momentum blurring in a generated diffraction profile and/or a poor detection rate because of the angular blurring.

Accordingly, it is desirable to calibrate and/or correct for focus point position inaccuracies to generate sharper diffraction profiles, as compared to images that include blurring from focus point position inaccuracies.

BRIEF DESCRIPTION OF THE INVENTION

In one aspect, a method for calibrating a detection system including a multi-focus X-ray source is provided. The method includes performing a scan of a calibration material using the detection system to acquire scan data, determining a diffraction profile of the calibration material using the scan data, deriving an actual scatter angle using the determined diffraction profile, deriving an offset angle using the determined actual scatter angle, storing the derived offset angle, and generating a table including the stored offset angle.

In another aspect, a detection system is provided. The detection system includes a multi-focus X-ray source including a plurality of focus points at which primary rays are generated by the multi-focus X-ray source and a scatter detection plane including a plurality of scatter detector elements. The plurality of scatter detector elements is configured to receive scattered radiation resulting from an interaction between the primary rays and a material. A control system is operatively coupled to the plurality of scatter detector elements. The control system is configured to perform a scan of a calibration material to acquire scan data from the plurality of scatter detector elements, determine a diffraction profile of the calibration material using the scan data, derive an actual scatter angle using the determined diffraction profile, derive an offset angle using the determined actual scatter angle, store the derived offset angle, and generate a table including the stored offset angle.

In yet another aspect, a method for correcting scan data of an unknown material is provided. The method includes performing a scan of the unknown material to acquire scan data using a detection system, determining an actual scatter angle of the unknown material using a table of known offset angles for a calibration material, and correcting the scan data of the unknown material using the determined actual scatter angle.

The embodiments described herein provide a calibration method and a correction method for accounting for deviations of focus point positions from a straight line. As such, the embodiments described herein substantially improve a detection rate and reduce a false alarm rate of the detection system described herein.

BRIEF DESCRIPTION OF THE DRAWINGS

FIG. 1 is a schematic view of an exemplary embodiment of a detection system substantially in an X-Y plane.

FIG. 2 is a schematic view of the detection system shown in FIG. 1 in an X-Z plane.

FIG. 3 is a schematic view of a portion of the detection system shown in FIGS. 1 and 2.

FIG. 4 is a flowchart of an exemplary calibration and correction method that may be used with the detection system shown in FIGS. 1-3.

DETAILED DESCRIPTION OF THE INVENTION

The embodiments described herein provide a calibration method and/or a correction method for accounting for inaccuracies of focus point positions with respect to a straight line. As such, the embodiments described herein substantially improve a detection rate and reduce a false alarm rate of the detection system described herein by generating a sharp diffraction profile of an unknown material.

While described in terms of detecting contraband including, without limitation, weapons, explosives, and/or narcotics, within checked or carry-on baggage, the embodiments described herein can be used for any suitable security detection or other X-ray diffraction imaging application, including applications in the plastics recycling, pharmaceutical, and/or non-destructive testing industries. Furthermore, angles and dimensions shown in the accompanying figures herein are not to scale, and may be exaggerated for clarity. Moreover, although as referred to herein, a diffraction profile and/or image is "generated," it should be understood that "generating" the diffraction profile and/or image includes generating and outputting the diffraction profile and/or image to any suitable device, such as a display device, a printing device, and/or a memory device.

Figure 1:
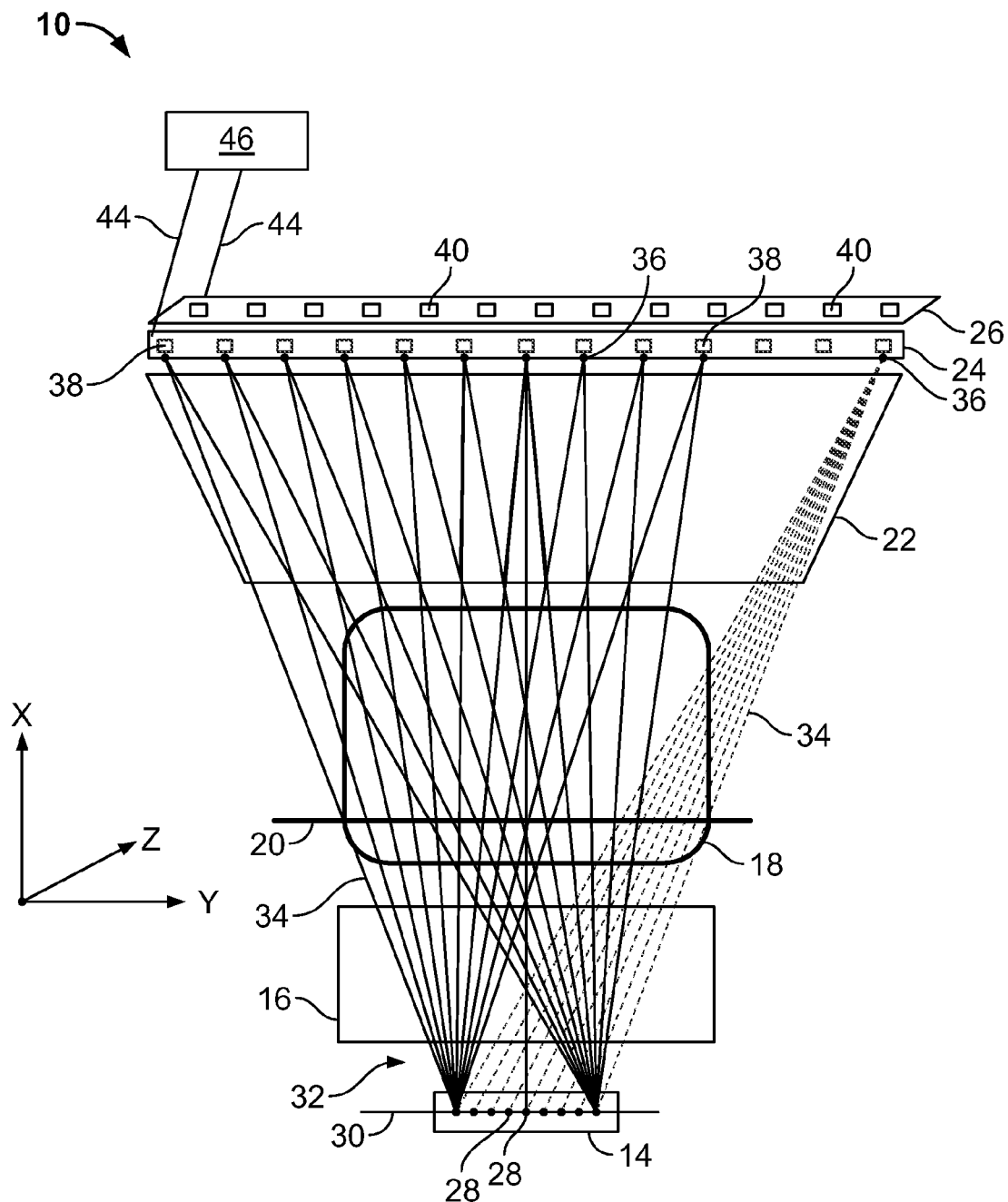
FIGS. 1-4 show exemplary embodiments of the system and methods described herein.
Figure 2:
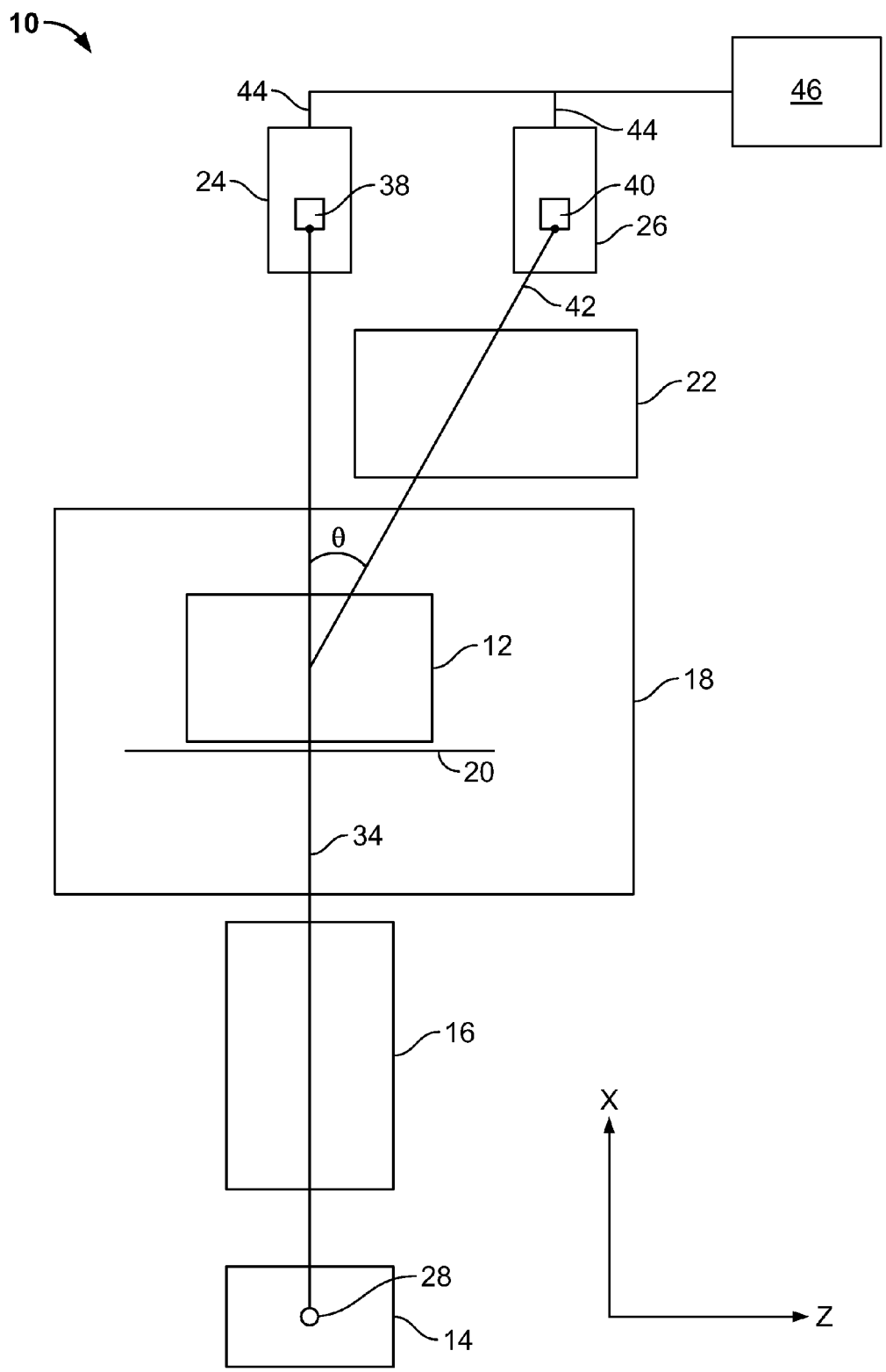

FIG. 1 is a schematic view of an exemplary detection system 10 in substantially an X-Y plane. FIG. 2 is a schematic view of detection system 10 in an X-Z plane. An object 12 located in detection system 10 is shown in FIG. 2, but object 12 is omitted from FIG. 1 for clarity. In the exemplary embodiment, security detection system 10 includes a multi-focus X-ray source (MFXS) 14, a primary collimator 16, an object space 18, a support 20, a secondary collimator 22, a transmission detector 24, and a scatter detector 26. Scatter detector 26 is offset in a Z-axis direction from transmission detector 24, as shown in FIG. 2.

In the exemplary embodiment, transmission detector 24 includes a plurality of detector elements 38. More specifically, detector elements 38 are each configured to detect radiation from primary rays 34 that are transmitted through object 12 within object space 18. Furthermore, scatter detector 26 includes a plurality of scatter detector elements 40. In the exemplary embodiment, scatter detector elements 40 are configured to detect coherent scattered radiation 42 generated when a primary ray 34 interacts with object 12. In one embodiment, detector elements 38 include charge integration detectors, and scatter detector elements 40 include pulse-counting energy-resolving detectors.

In the exemplary embodiment, MFXS 14 is located on a lower support surface, such as a floor, while transmission detector 24 and scatter detector 26 are located on an upper support structure, such as a ceiling. In an alternative embodiment, MFXS 14 is located on the upper support structure, and transmission detector 24 and scatter detector 26 are located on the lower support surface. Furthermore, in the exemplary embodiment, MFXS 14, transmission detector 24, and scatter detector 26 are stationary, and support 20 is a conveyor belt capable of movement backward and forward in a direction substantially parallel to a Z-axis. In the exemplary embodiment, object space 18 is defined between transmission detector 24 and MFXS 14. In one embodiment, object space 18 is a baggage tunnel through which the conveyor belt moves. In an alternative embodiment, MFXS 14, transmission detector 24, and scatter detector 26 are capable of coordinated movement at least in a direction substantially parallel to the Z-axis, and support 20 is stationary. In certain alternative embodiments, MFXS 14, transmission detector 24, scatter detector 26, and support 20 are each capable of moving.

Figure 3:
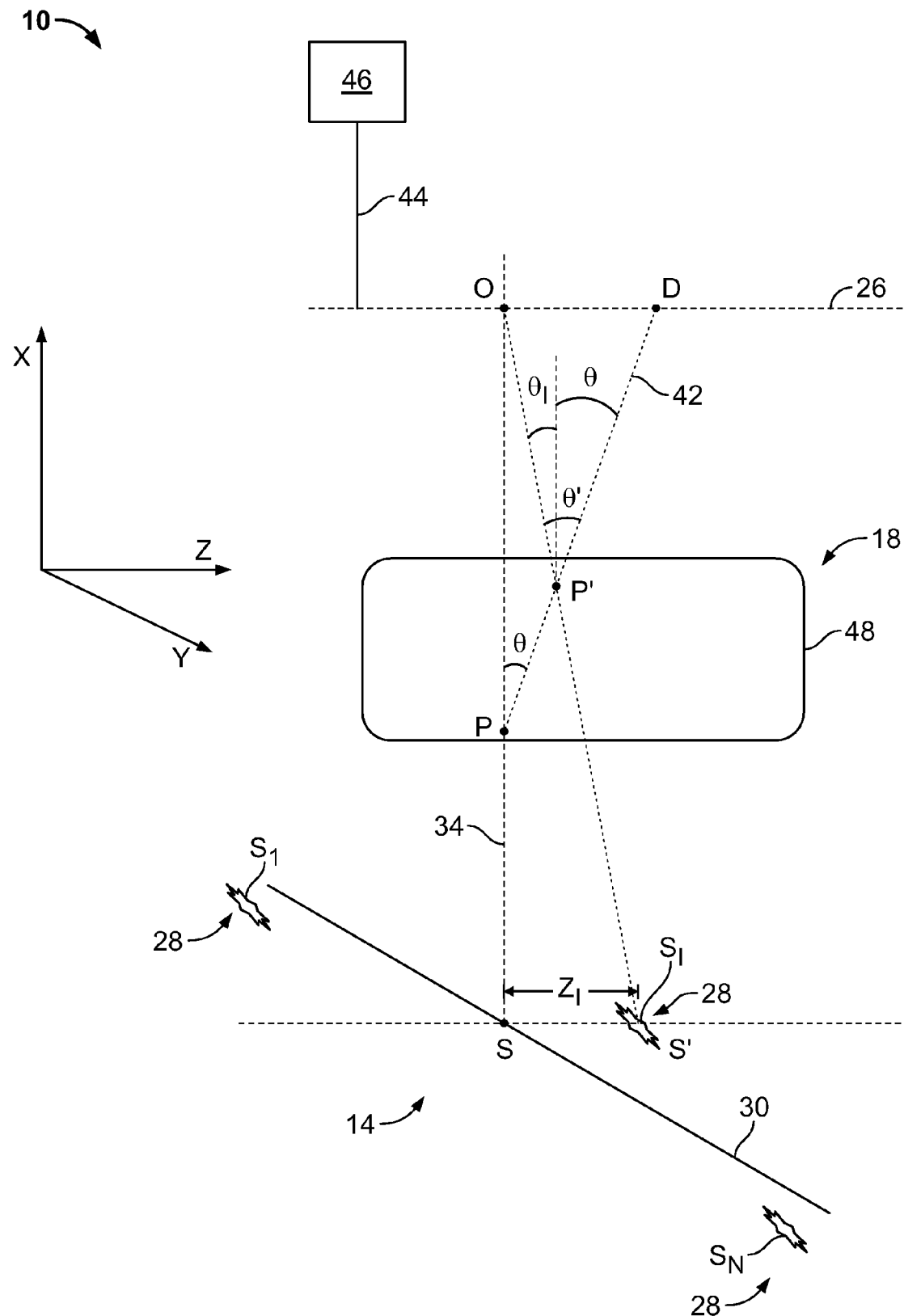

In the exemplary embodiment, MFXS 14 is configured to emit X-ray radiation sequentially or simultaneously from a plurality of focus points 28 distributed along MFXS 14 in a direction substantially parallel to a Y-axis. In the exemplary embodiment, MFXS 14 has focus points 28 $S_1 \ldots S_N$, wherein N is the number of focus points and $S_I$ is a focus point between focus point $S_1$ and focus point $S_N$. In the exemplary embodiment, N is any suitable number that enables detection system 10 to function as herein described. In one embodiment, N is equal to any number between and including 10 and 20. In the exemplary embodiment, detection system 10 is designed such that each focus point 28 lies at a point, such as point S (shown in FIG. 3), on a straight line 30 that is substantially parallel to the Y-axis. However, due to manufacturing tolerances and/or thermo-mechanical effects, focus points 28 may not all lie along straight line 30 and may be offset from a respective point on line 30, as shown in FIG. 3.

Referring to FIGS. 1 and 2, MFXS 14 is, in the exemplary embodiment, configured to emit, through primary collimator 16, a set 32 of primary rays 34 of radiation from each focus point 28. In one embodiment, primary rays 34 are X-ray pencil beams generated from each focus point 28 of MFXS 14. More specifically, in the exemplary embodiment, each primary ray 34 of each set 32 is directed at a corresponding target point 36 of a plurality of target points 36 which lie in the same X-Y plane as MFXS 14. Further, each target point 36 is positioned at the same X coordinate value, but at different Y coordinate values. In the exemplary embodiment, each target point 36 is located at a detector element 38 of transmission detector 24. As such, each detector element 38 is configured to detect one primary ray 34 from each focus point 28.

A portion of the X-ray radiation from each primary ray 34 typically is scattered in various directions upon interaction with object 12 in object space 18. Secondary collimator 22 is configured to facilitate ensuring that a portion of scattered radiation 42 arriving at each scatter detector element 40 has a constant scatter angle θ with respect to corresponding primary ray 34 from which scattered radiation 42 originated. For example, secondary collimator 22 is configured to absorb scattered radiation that is not parallel to the direction of scattered radiation 42. Further, although in the exemplary embodiment secondary collimator 22 and scatter detector elements 40 are positioned on one side of primary rays 34 with respect to the Z-axis, in alternative embodiments secondary collimator 22 and scatter detector elements 40 may be positioned on the other side, or on both sides, of primary rays 34 with respect to the Z-axis.

In the exemplary embodiment, transmission detector 24 and scatter detector 26 are in electronic communication with a number of channels 44, for example, N number of channels $C_1, \ldots C_N$, wherein N is selected based on the configuration of security detection system 10. Channels 44 electronically communicate data collected by transmission detector 24 and each scatter detector element 40 to a control system 46. In the exemplary embodiment, control system 46 combines an output from transmission detector 24 and outputs from scatter detector elements 40 to generate information about object 12 within object space 18. For example, but not by way of limitation, control system 46 may generate multi-view projections, section images, and/or an X-ray diffraction profile of object 12 to facilitate identifying a location in the container of specific materials detected by XDI analysis.

Figure 4:
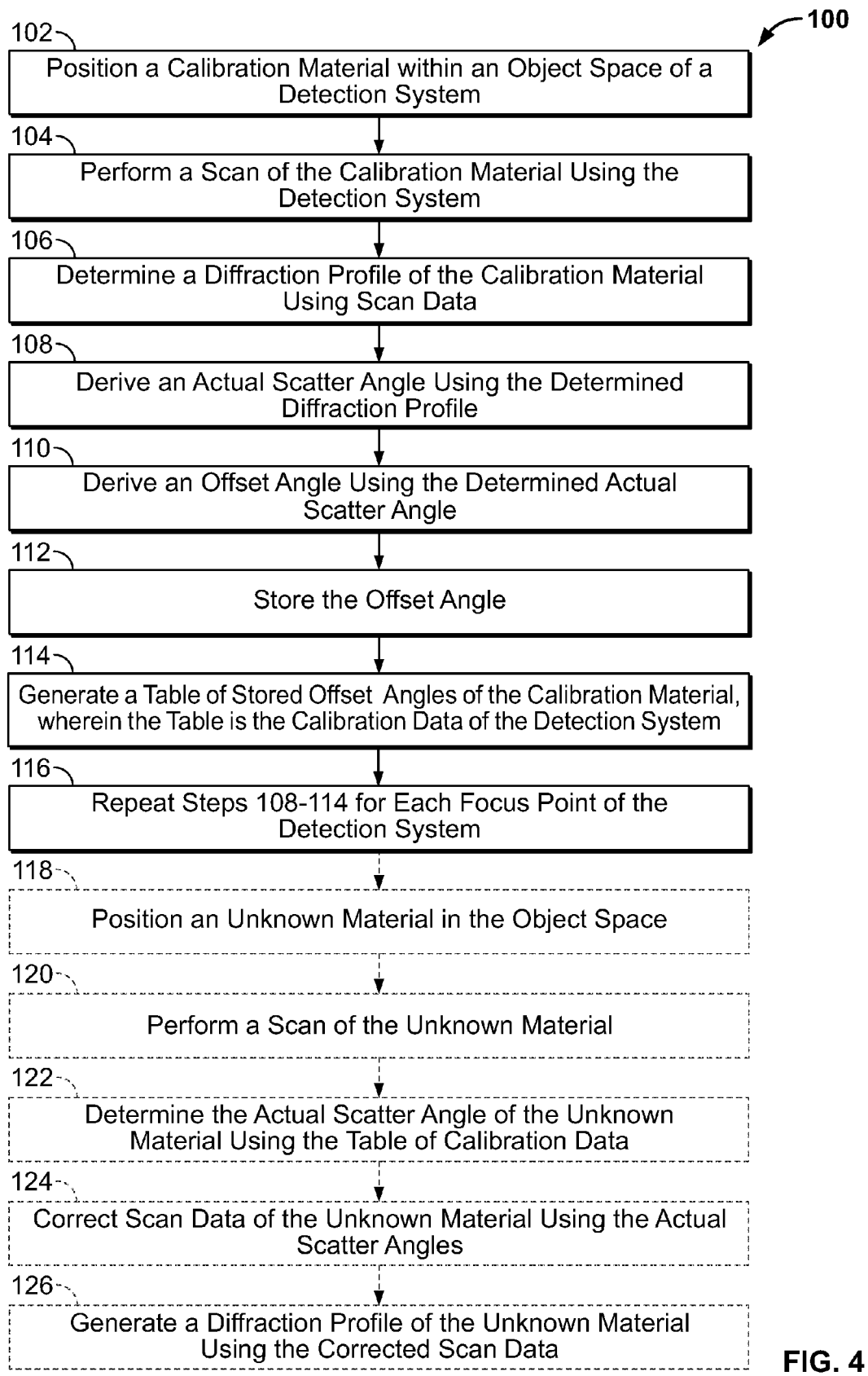

FIG. 3 is a schematic view of a portion of detection system 10. FIG. 4 is a flowchart of an exemplary calibration and correction method 100 that may be performed using detection system 10. The calibration portion of method 100 is shown in solid lines, and the correction portion of method 100 is shown in dashed lines. In one embodiment, the calibration portion of method 100 is performed without performing the correction portion of method 100. In an alternative embodiment, the correction portion of method 100 is performed without performing the calibration portion of method 100.

When primary rays 34 are transmitted through primary collimator 16, only those primary rays 34 converging on a focus point O are allowed to enter object space 18. As such, primary rays 34 propagate through an object, such as object 12 and/or calibration material 48, and induce scatter events, for example, at a point P within calibration material 48, that generate scatter rays 42. In the exemplary embodiment, point P is a point in calibration material 48 from which radiation scatters in an ideal situation, wherein, in the ideal situation, all focus points 28 are on straight line 30. From point P, scatter rays 42 are collimated by secondary collimator 22 to arrive at a point D on scatter detector 26.

In the exemplary embodiment, each focus point 28 is sequentially activated from focus point $S_1$, through focus point $S_I$ to focus point $S_N$ and, in principle, all focus points 28 should lie on straight line 30 that is substantially parallel to the Y-axis. For primary ray 34 from focus point $S_I$, positioned at a point S on line 30, it is possible that focus point $S_I$ does not actually lie on line 30 at point S, but is displaced a certain distance $Z_I$ from line 30 at a point S'. As such, an angle of scatter, or scatter angle, is not angle ∠OPD (θ) but is angle ∠OP'D (θ'), wherein P' is the actual point in calibration material 48 from which primary ray 34 is scattering. Such a change in the scatter angle causes a change in a momentum transfer x corresponding to a certain photon energy E, as given in the following formula:

$$x = \frac{E}{hc} \sin\left(\frac{\theta'}{2}\right),$$ (Eq. 1)

wherein h is Planck's constant and c is the speed of light. The photon energy E is measured by the energy-resolving scatter detector elements 40 (shown in FIGS. 1 and 2). When a known material is within object space 18, Equation 1 can be solved to find actual scatter angle θ' because, if the material is known, the momentum transfer x of the material is also known.

In the exemplary embodiment, control system 46 is configured to determine the actual scatter angle θ' corresponding to focus point $S_I$ that does not lie on straight line 30 to calibrate detection system 10. More specifically, the calibration portion of method 100 includes positioning 102 calibration material 48 having known, sharp diffraction Bragg peaks, such as polyethylene, sodium chloride (NaCl), or aluminium (Al), in object space 18. A scan of calibration material 48 is performed 104 using detection system 10 to acquire scan data. Control system 46 determines 106 a diffraction profile of calibration material 48 for a first focus point $S_I$. Control system 46 is configured to then derive 108 the actual scatter angle θ' from Equation 1 on the basis of the known positions of the Bragg peaks of calibration material 48, as shown in the determined diffraction profile.

Once the actual scatter angle θ' is known by solving Equation 1 for θ', control system 46 is configured to derive 110 an offset angle $\theta_I$ of focus point $S_I$, using the following equation:

$$\theta_I = \theta' - \theta.$$ (Eq. 2)

The derived offset angle $\theta_I$ is then stored 112 within control system 46, and a table of values of offset angles $\theta_I$ of the calibration method is generated 114. Generation 114 of the table includes not only generating the table, but outputting the table to any suitable device, such as a display device, a printing device, and/or a memory device.

In one embodiment, the above-described procedure is repeated 116 by control system 46 for each focus point 28, $S_1$, $S_2$ ... $S_I$ ... $S_N$, using the scan data, such that a respective offset angle $\theta_I$ is found for each focus point 28. Each offset angle $\theta_I$ is stored 112 in the table within control system 46. The stored table includes all determined values of the offset angles $\theta_I$ of focus points 28. More specifically, the table of values includes the offset angle $\theta_I$ for each focus point 28 within MFXS 14. The table of values is the calibration data for calibrating detection system 10.

After the calibration data is generated 114, the correction portion of method 100 may be performed using the table of calibration data. More specifically, during the correction portion of method 100, an unknown material of object, such as object 12, is positioned 118 within object space 18. A scan of the unknown material is performed 120 using detection system 10 to acquire scan data. Control system 46 determines 122 the actual scatter angles θ' for the unknown material using the values of the offset angles $\theta_I$ in the table of calibration data and Equation 2. The actual scatter angles θ' are then used to correct 124 the acquired scan data of the unknown material to be at the ideal scatter angle θ. More specifically, each offset angle $\theta_I$ in the table is subtracted from a corresponding actual scatter angle θ' of the unknown material to determine the ideal scatter angle θ at each focus point 28. A diffraction profile of the unknown material is then generated 126 by control system 46 using the corrected scan data. Generation 126 of the diffraction profile includes not only generating the diffraction profile, but outputting the diffraction profile to any suitable device, such as a display device, a printing device, and/or a memory device. The unknown material can then be identified using the generated diffraction profile by any suitable method.

Accordingly, a diffraction profile generated 126 using the corrected data has an improved resolution, as compared to diffraction profiles generated from data that are not corrected for inaccuracies in focus point positions. Further, the calibration data can be used to scan a series of unknown materials. Moreover, the above-described calibration portion of method 100 can be repeated at regular intervals, such as once every hour, to account for time-dependent inaccuracies in the positions of focus points 28.

The above-described system and method facilitate correcting scan data for inaccuracies in focus point positions. More specifically, by knowing the actual scatter angles of the unknown material, improved resolution in the diffraction profile can be achieved, as compared to methods and system that do not correct scan data for inaccuracies in focus point positions. Accordingly, the embodiments described herein produce sharper, more accurate diffraction profiles which increase a detection rate and reduce a false alarm rate of the detection system described herein, as compared to systems that do not correct scan data for inaccuracies in focus point positions. As such, the performance of the detection system described herein is improved, as compared to methods and system that do not correct scan data for inaccuracies in focus point positions.

A technical effect of the system and method described herein includes at least one of (a) determining a diffraction profile of a calibration material using scan data, (b) deriving an actual scatter angle using a determined diffraction profile, (c) deriving an offset angle using a determined actual scatter angle, (d) storing a derived offset angle, (e) generating a table including a stored offset angle, wherein the table includes calibration data for a detection system, and (f) correcting scan data of an unknown material using a table of stored offset angles of a calibration material.

Exemplary embodiments of methods and a system for calibrating and correcting a detection system are described above in detail. The methods and system are not limited to the specific embodiments described herein, but rather, components of system and/or steps of the methods may be utilized independently and separately from other components and/or steps described herein. For example, the methods may also be used in combination with other imaging systems and methods, and are not limited to practice with only the detection system and methods as described herein. Rather, the exemplary embodiment can be implemented and utilized in connection with many other imaging applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for calibrating a detection system including a multi-focus X-ray source, said method comprising:
    performing a scan of a calibration material using the detection system to acquire scan data;
    determining a diffraction profile of the calibration material using the scan data;
    deriving an actual scatter angle using the determined diffraction profile;
    deriving an offset angle using the determined actual scatter angle;
    storing the derived offset angle; and
    generating a table including the stored offset angle.

2. A method in accordance with claim 1, wherein performing a scan of a calibration material comprises performing a scan of a material having a diffraction profile with known, sharp diffraction Bragg peaks.

3. A method in accordance with claim 1, wherein deriving an actual scatter angle using the determined diffraction profile comprises deriving the actual scatter angle using the equation:

$$x = \frac{E}{hc}\sin\left(\frac{\theta'}{2}\right),$$

wherein $\theta'$ is the actual scatter angle, x is a known momentum transfer of the calibration material, E is a photon energy measured during the performance of the scan, h is Planck's constant, and c is the speed of light.

4. A method in accordance with claim 1, wherein deriving an offset angle using the determined actual scatter angle comprises deriving the offset angle using the equation:

$$\theta_f = \theta' - \theta,$$

wherein $\theta_f$ is the offset angle, $\theta'$ is the actual scatter angle, and $\theta$ is an ideal scatter angle.

5. A method in accordance with claim 1, wherein generating a table including the stored offset angle comprises:
    deriving an actual scatter angle for each focus point of a plurality of focus points of the multi-focus X-ray source using the determined diffraction profile;
    deriving an offset angle for each focus point using a respective determined actual scatter angle; and
    storing the derived offset angle for each focus point.

6. A method in accordance with claim 1, further comprising correcting scan data of an unknown material using the generated table.

7. A method in accordance with claim 6, wherein correcting scan data of an unknown material comprises:
    performing a scan of the unknown material using the detection system to acquire scan data of the unknown material;
    determining an actual scatter angle of the unknown material using the generated table; and
    correcting the scan data of the unknown material using the determined actual scatter angle of the unknown material.

8. A method in accordance with claim 6, wherein correcting scan data of the unknown material comprises generating a diffraction profile of the unknown material using the corrected scan data.

9. A detection system comprising:
    a multi-focus X-ray source comprising a plurality of focus points at which primary rays are generated by said multi-focus X-ray source;
    a scatter detection plane comprising a plurality of scatter detector elements, said plurality of scatter detector elements configured to receive scattered radiation resulting from an interaction between said primary rays and a material; and
    a control system operatively coupled to said plurality of scatter detector elements, said control system configured to:
        perform a scan of a calibration material to acquire scan data from said plurality of scatter detector elements;
        determine a diffraction profile of the calibration material using the scan data;
        derive an actual scatter angle using the determined diffraction profile;
        derive an offset angle using the determined actual scatter angle;
        store the derived offset angle; and
        generate a table including the stored offset angle.

10. A detection system in accordance with claim 9, wherein said control system is further configured to:
    derive an actual scatter angle for each focus point of said plurality of focus points using the determined diffraction profile;
    derive an offset angle for each focus point using the determined actual scatter angle;
    store the derived offset angle for each focus point in the table.

11. A detection system in accordance with claim 9, wherein said control system is further configured to:
    perform a scan of an unknown material to acquire scan data from said plurality of scatter detector elements;
    determine an actual scatter angle of the unknown material using the generated table; and
    correct the scan data of the unknown material using the determined actual scatter angle of the unknown material.

12. A detection system in accordance with claim 9, wherein said plurality of focus points are aligned with respect to a straight line through said multi-focus X-ray source.

13. A detection system in accordance with claim 9, wherein said control system in further configured to derive the actual scatter angle using a momentum transfer of the calibration material and a photon energy detected by said plurality of scatter detector elements.

14. A detection system in accordance with claim 9, wherein said control system in further configured to derive an offset angle using the determined actual scatter angle and an ideal scatter angle.

15. A method for correcting scan data of an unknown material, said method performed using a detection system having a control system, said method comprising:
    performing a scan of the unknown material to acquire scan data using the detection system;
    determining, using the control system, an actual scatter angle of the unknown material using a table of known offset angles for a calibration material; and
    correcting, using the control system, the scan data of the unknown material using the determined actual scatter angle.

16. A method in accordance with claim 15, further comprising generating, using the control system, a diffraction profile of the unknown material using the corrected scan data.

17. A method in accordance with claim 15, wherein determining an actual scatter angle of the unknown material using a table of known offset angles for a calibration material comprises subtracting a known offset angle in the table from the determined actual scatter angle of the unknown material to determine an ideal scatter angle.

18. A method in accordance with claim 15, further comprising generatin, using the control system, the table of known offset angles for the calibration material by:
  performing a scan of the calibration material using the detection system to acquire scan data of the calibration material;
  determining a diffraction profile of the calibration material using the scan data of the calibration material;
  deriving an actual scatter angle using the determined diffraction profile;
  deriving an offset angle using the determined actual scatter angle; and
  storing the derived offset angle in the table.

19. A method in accordance with claim 18, wherein deriving an actual scatter angle using the determined diffraction profile comprises deriving the actual scatter angle using a momentum transfer of the calibration material and a photon energy detected by the detection system.

20. A method in accordance with claim 18, wherein deriving an offset angle using the determined actual scatter angle comprises deriving the offset angle using the determined actual scatter angle and an ideal scatter angle.

* * * * *